United States Patent
Kuznik et al.

(10) Patent No.: US 12,329,461 B2
(45) Date of Patent: Jun. 17, 2025

(54) SYSTEM AND METHOD FOR ALIGNING A TOOL WITH AN AXIS TO PERFORM A MEDICAL PROCEDURE

(71) Applicant: THINK Surgical, Inc., Fremont, CA (US)

(72) Inventors: Kyle Kuznik, Livermore, CA (US); Micah Forstein, Topeka, KS (US); Daniel Bonny, San Francisco, CA (US)

(73) Assignee: THINK Surgical, Inc., Fremont, CA (US)

( * ) Notice: Subject to any disclaimer, the term of this patent is extended or adjusted under 35 U.S.C. 154(b) by 477 days.

(21) Appl. No.: 17/782,031

(22) PCT Filed: Dec. 1, 2020

(86) PCT No.: PCT/US2020/062686
§ 371 (c)(1),
(2) Date: Jun. 2, 2022

(87) PCT Pub. No.: WO2021/113227
PCT Pub. Date: Jun. 10, 2021

(65) Prior Publication Data
US 2023/0000558 A1    Jan. 5, 2023

Related U.S. Application Data

(60) Provisional application No. 62/942,341, filed on Dec. 2, 2019.

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/20* (2016.02); *A61B 34/70* (2016.02); *A61B 34/30* (2016.02)

(58) Field of Classification Search
CPC ......... A61B 34/10; A61B 34/20; A61B 34/30; A61B 34/70; A61B 2034/107
(Continued)

(56) References Cited

U.S. PATENT DOCUMENTS

| | | | |
|---|---|---|---|
| 4,257,411 A | 3/1981 | Cho | |
| 4,739,751 A | 4/1988 | Sapega et al. | |

(Continued)

FOREIGN PATENT DOCUMENTS

| | | |
|---|---|---|
| JP | 2007-029486 | 2/2007 |
| WO | WO 2017/055990 | 4/2017 |

(Continued)

OTHER PUBLICATIONS

Hosseini, A. et al., Tunnel position and graft orientation in failed anterior cruciate ligament reconstruction: a clinical and imaging analysis, International Orthopaedics, Aug. 2011, vol. 36, pp. 845-852.

(Continued)

*Primary Examiner* — Jessica Weiss
(74) *Attorney, Agent, or Firm* — Pandiscio & Pandiscio

(57) ABSTRACT

A system and method are provided for aligning a tool with a targeted axis in tissue to perform a medical procedure. A medical plan is registered to the location of the tissue using a computer-assisted medical system, where the medical plan include a planned position for the targeted axis based on pre-procedure data. The tool is aligned with the planned position for the targeted axis using a computer-assisted medical system. The computer-assisted medical system includes a hand-held device having a handle and a working portion adjustable relative to the handle so as to orient the tool. A computing system is also provided comprising a tracking system and a control system for registering the medical plan to the location of the tissue, tracking the (Continued)

hand-held device relative to the tissue and the medical plan, and adjusting the working portion of the hand-held device relative to its handle.

15 Claims, 11 Drawing Sheets

(51) Int. Cl.
*A61B 34/20* (2016.01)
*A61B 34/30* (2016.01)

(58) Field of Classification Search
USPC ........................................ 606/96, 104, 79–86
See application file for complete search history.

(56) References Cited

U.S. PATENT DOCUMENTS

| | | |
|---|---|---|
| 5,086,401 A | 2/1992 | Glassman et al. |
| 6,033,415 A | 3/2000 | Mittelstadt et al. |
| 6,061,644 A | 5/2000 | Leis |
| 6,322,567 B1 | 11/2001 | Mittelstadt et al. |
| 7,043,961 B2 | 5/2006 | Pandey et al. |
| 7,206,626 B2 | 4/2007 | Quaid, III |
| 7,972,341 B2 | 7/2011 | Berberich et al. |
| 8,010,177 B2 | 8/2011 | Csavoy et al. |
| 8,287,522 B2 | 10/2012 | Moses et al. |
| 8,876,830 B2 | 11/2014 | Hodorek et al. |
| 8,961,536 B2 | 2/2015 | Nikou et al. |
| 9,060,794 B2 | 6/2015 | Kang et al. |
| 9,119,638 B2 | 9/2015 | Schwarz et al. |
| 10,492,870 B2 | 12/2019 | Shalayev et al. |
| 11,457,980 B2 * | 10/2022 | Bonny ............... A61B 17/1764 |
| 2011/0319913 A1 | 12/2011 | Labadie et al. |
| 2012/0143084 A1 | 6/2012 | Shoham |
| 2012/0254750 A1 | 10/2012 | Chessher |
| 2012/0294498 A1 * | 11/2012 | Popovic ............... A61B 1/0005 |
| | | 382/128 |
| 2013/0060278 A1 | 3/2013 | Bozung et al. |
| 2016/0135816 A1 | 5/2016 | Lavallee et al. |
| 2017/0245945 A1 | 8/2017 | Zuhars et al. |
| 2018/0344409 A1 * | 12/2018 | Bonny ................... A61B 34/20 |
| 2019/0021800 A1 * | 1/2019 | Crawford ............... A61B 34/20 |
| 2019/0069955 A1 * | 3/2019 | Popovic ................. A61B 34/20 |
| 2019/0254750 A1 * | 8/2019 | Metz ...................... A61B 6/505 |

FOREIGN PATENT DOCUMENTS

| | | | |
|---|---|---|---|
| WO | WO-2017091380 A1 * | 6/2017 | ........... A61B 17/154 |
| WO | WO-2018175172 A1 * | 9/2018 | ......... A61B 17/1626 |
| WO | WO 2020/257444 | 12/2020 | |
| WO | WO 2021/011646 | 1/2021 | |

OTHER PUBLICATIONS

Wagner et al., Disturbance Feed Forward Control of a Handheld Parallel Robot, Proceedings of the Fourth International Conference on Informatics in Control, Automation and Robotics, 2007, pp. 44-51.

Wagner et al., Control of a Handheld Robot for Orthopedic Surgery, IFAC Proceedings Volumes, Sep. 2004, vol. 37, Issue 14, pp. 477-482.

* cited by examiner

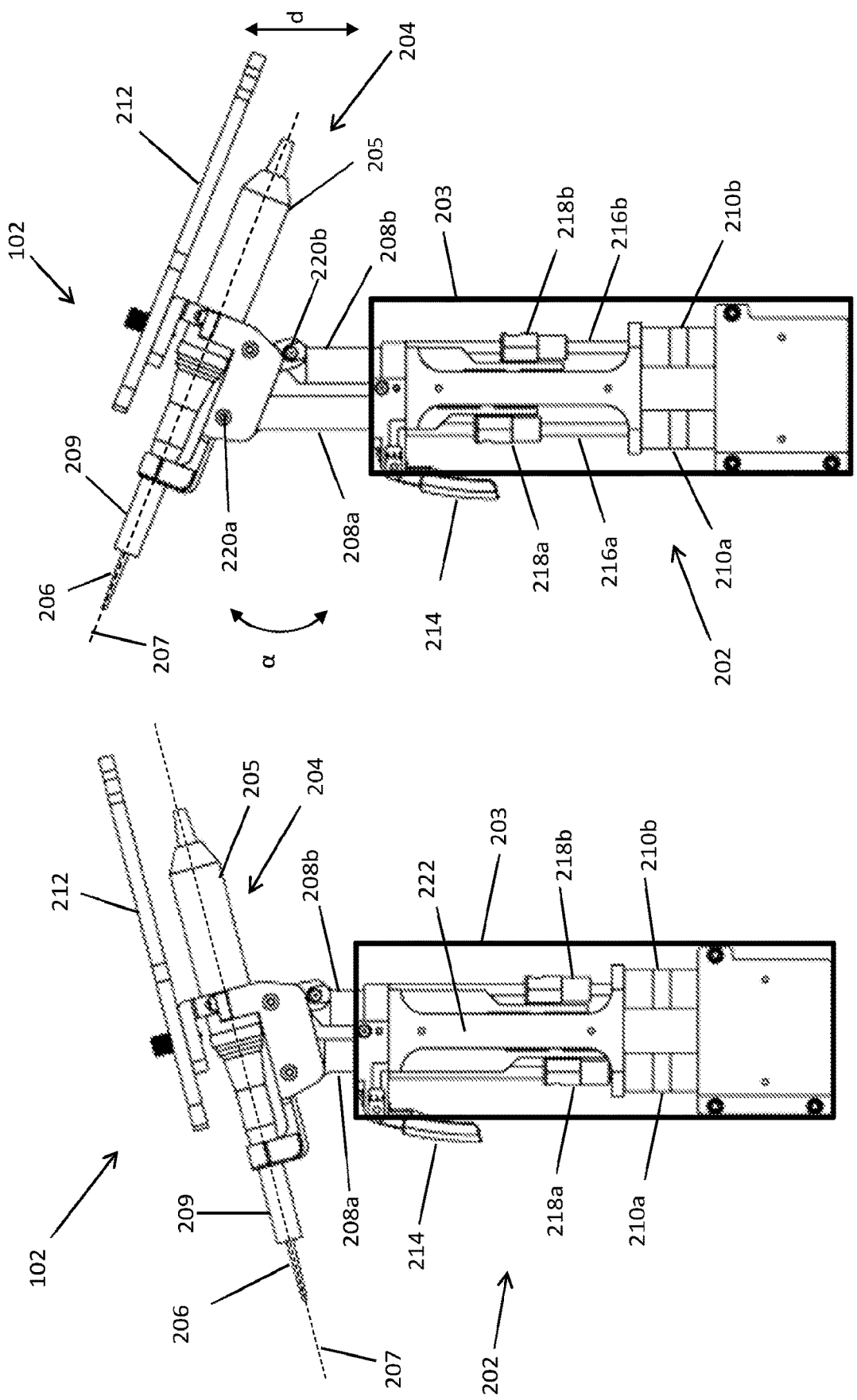

SYSTEM AND METHOD FOR ALIGNING A TOOL WITH AN AXIS TO PERFORM A MEDICAL PROCEDURE

REFERENCE TO PENDING PRIOR PATENT APPLICATION

This patent application claims benefit of pending prior U.S. Provisional Patent Application Ser. No. 62/942,341, filed Dec. 2, 2019 by THINK Surgical, Inc. and Kyle Kuznik for SYSTEM AND METHOD FOR CREATING BONE TUNNELLS FOR USE IN LIGAMENT AND/OR TENDON RECONSTRUCTION SURGERY, which patent application is hereby incorporated herein by reference.

TECHNICAL FIELD

The present invention relates to the field of computer-assisted and/or robotic medical procedures in general, and more particularly to systems and methods for accurately aligning a tool with a targeted axis in tissue with the aid of a computer-assisted medical device to perform a medical procedure.

BACKGROUND

Several medical procedures require the alignment of a tool with an axis to perform a medical procedure. For example, ligament reconstruction requires the alignment of a drill with an axis to form a tunnel in a bone to receive a ligament therein; biopsies require the alignment of a needle with an axis to reach a targeted location of tissue to be biopsied; spinal reconstruction requires the use of pedicle screws inserted with an axis in the pedicles of the vertebrae; and radiation treatments require the alignment of photon beams with an axis to reach a targeted tissue location for cancer therapy. These types of medical procedures all rely on the precise and accurate alignment of the tool to ensure a successful outcome.

One particular medical application requiring the alignment of a tool with an axis is the drilling of tunnels in bone for anterior cruciate ligament (ACL) reconstruction procedures. Rupture of the ACL is one of the most frequent injuries to the knee joint. ACL reconstruction is a common orthopedic procedure performed to repair the knee joint. Early stabilization of the knee joint by ACL reconstruction also decreases the risk of injury to other important structures.

The goal of anterior cruciate ligament (ACL) reconstruction procedures (as well as other similar ligament and tendon repairs used to repair other joints, including the elbow) is to replace a ruptured ligament or tendon with a graft that provides mechanical stability similar to the mechanical stability of the native anatomy while preserving the range of motion of the knee (or other) joint. However, the native cruciate ligature of the knee is highly complex, and presents several challenges for successful reconstruction procedures.

During ACL reconstruction procedures a graft is placed into roughly the same location that the native ACL occupied prior to rupture. To achieve this "colocation" with a graft, holes (i.e., bone tunnels) are drilled along an axis in the femur and tibia in order to approximate the "footprint" of the native ACL. A graft is placed in these tunnels, and fixated by some means (e.g., anchors, cross-pins, etc.) to the bone on both ends. The graft is intended to restore stability to the injured knee, while maintaining range of motion.

However, the most significant challenge in ACL reconstruction is typically achieving the exact, correct placement of drilled bone tunnels (i.e., the holes drilled in the femur and tibia to receive the graft). When the holes are incorrectly placed (i.e., not drilled in the bone in the precise, correct location), the outcome of surgery is significantly affected. By way of example but not limitation, poor bone tunnel placement can result in restricted range of motion, knee joint instability, reaction of the synovium in the knee, and/or knee joint pain. Furthermore, impingement of the graft (e.g., in the femoral notch during movement of the joint) and/or improper graft tension may result in potential graft failure with lesion development. A study entitled "Tunnel position and graft orientation in failed anterior cruciate ligament reconstruction: a clinical and imaging analysis" (Ali Hosseini et al., International Orthopaedics 2012 April; 36(4): 845-852) confirmed that technical errors in the positioning of graft tunnels is the most common problem arising in ACL reconstruction. The study quantitatively evaluated femoral and tibial tunnel positions and intra-articular graft orientation of primary ACL reconstruction in patients who had undergone revision ACL reconstruction, and found that non-anatomically correct (i.e., incorrectly positioned) tunnel and graft orientation was a primary cause of graft failure. It was further determined that the sagittal elevation angle for failed ACL reconstruction grafts (69.6°±13.4°) was significantly greater ($p<0.05$) than that of the native anteromedial (AM) and posterolateral (PL) bundles of the ACL (AM 56.2°±6.1°, PL 55.5°±8.1°). In the transverse plane, the deviation angle of the failed graft (37.3°±21.0°) was significantly greater than native ACL bundles.

Precisely placed bone tunnels are difficult to achieve through current surgical methods. Conventional techniques for ACL reconstruction include the use of hand-held instrumentation (e.g., drill guides) to align a hand-held drill in the desired tunnel placement, such as the tools described in U.S. Pat. Nos. 4,257,411; 4,739,751; and 7,972,341. Alignment of the hand-held instruments and the drill is particularly difficult because ACL reconstruction surgery is predominantly performed arthroscopically, and hence access to (and visualization of) both the femur and the tibia is typically limited by the surrounding anatomy. Arthroscopy provides a limited view of the anatomical structures and does not allow the surgeon to gain a complete 3D view of important anatomical structures. During bone tunnel drilling, changes in bone density and/or uneven and/or slippery surfaces of the boney surfaces make hand-held drilling difficult. Furthermore, ACL reconstructions generally require surgical skills that present a high learning curve, and mastery is generally attainable only from high volumes of surgery and extensive experience. ACL reconstructions are therefore most often performed by experienced orthopedic surgeons. It is estimated that up to 20% of ACL grafts fail due to impingement, improper graft tension, or poor tunnel placement.

In addition to ACL reconstruction, there are several other medical procedures that require the alignment of a tool with one or more axes. Notable examples include: a) aligning a biopsy needle with an axis to reach a targeted tissue location for bone biopsies, brain biopsies, lung biopsies, etc.; b) aligning a syringe needle with an axis to reach a targeted tissue location for the delivery of medication, markers, or other injectables to a targeted tissue location in the brain, spine, lung, etc.; b) inserting fixation devices, for example, pins, nails, or screws, with an axis for spinal applications, fracture plates, bone reconstruction, etc.; c) laser, carbon dioxide, radiation, ablation, or radiofrequency treatment of tissues along one or more axes or to reach one or more targeted tissue locations along the axes; and d) any other procedure requiring the alignment of a tool with one or more axes to perform a medical procedure. For any of these procedures, accuracy and precision is paramount to a successful outcome, where computer-assisted medical systems can play a key role to ensure that success.

Thus, there exists a need for a new and improved system and method to facilitate accurate alignment of a tool with an axis to perform a medical procedure. There is a more specific need for aligning a tool with an axis for the drilling of tunnels in a bone along the axis for ligament and/or tendon reconstruction surgery which improves clinical outcomes.

SUMMARY OF THE INVENTION

The present invention comprises the provision and use of a system and method for aligning a tool with an axis to perform a medical procedure on tissue.

In one preferred form of the invention, there is provided a method for aligning a tool with a targeted axis to perform a medical procedure on tissue, the method comprising:

registering a medical plan to the location of the tissue using a computer-assisted medical system, wherein the medical plan includes a planned position for the targeted axis based on pre-procedure data; and aligning, with a computer-assisted medical system, the tool with the planned position for the targeted axis registered to the tissue.

In another preferred form of the invention, there is provided a system for aligning a tool with a targeted axis in tissue to perform a medical procedure, the system comprising:

a medical plan generated with planning software executed on a computer, wherein the medical plan includes a planned position for a targeted axis based on pre-procedure data;

a hand-held device for aligning the tool relative to the planned position for the targeted axis, the hand-held device comprising a handle and a working portion adjustable relative to the handle so as to orient the tool; and a computing system comprising a tracking system and a control system, wherein said computing system: (i) registers the medical plan to the location of the tissue; (ii) tracks the hand-held device relative to the tissue and the medical plan; and (iii) adjusts the position of the working portion on the hand-held device relative to its handle so that the tool is aligned with the planned position for the targeted axis defined in the medical plan.

In another preferred form of the invention, there is provided a hand-held device for aligning a tool coupled to the device to a targeted axis included in a medical plan for tissue generated using pre-procedure data to perform a medical procedure, the device comprising:

a handle;

a working portion connected to the handle and including a coupler for removable connection to the tool, wherein the position of the working portion is adjustable relative to the position of the handle so as to move the tool relative to the handle;

a receiver for receiving signals from a computing system capable of registering the medical plan to tissue and tracking the location of the device relative to the tissue and the medical plan; and an actuator for moving the working portion relative to the handle based on the received signals such that the tool is aligned with the targeted axis.

BRIEF DESCRIPTION OF THE DRAWINGS

The present invention is further detailed with respect to the following drawings that are intended to show certain aspects of the present of invention, but should not be construed as a limit on the practice of the invention, wherein:

FIGS. 2A and 2B are schematic views showing a two-degree-of-freedom articulating hand-held device of the computer-assisted medical system shown in FIG. 1, wherein FIG. 2A illustrates the hand-held device in a first position and orientation, and wherein FIG. 2B illustrates the hand-held device in a second position and orientation;

FIGS. 6A and 6B are schematic views showing a virtual bone model and a planned position for a bone tunnel, wherein FIG. 6A is a schematic perspective view of the virtual bone model, and FIG. 6B is a sagittal view of the virtual bone model;

DETAILED DESCRIPTION

Figure 1:
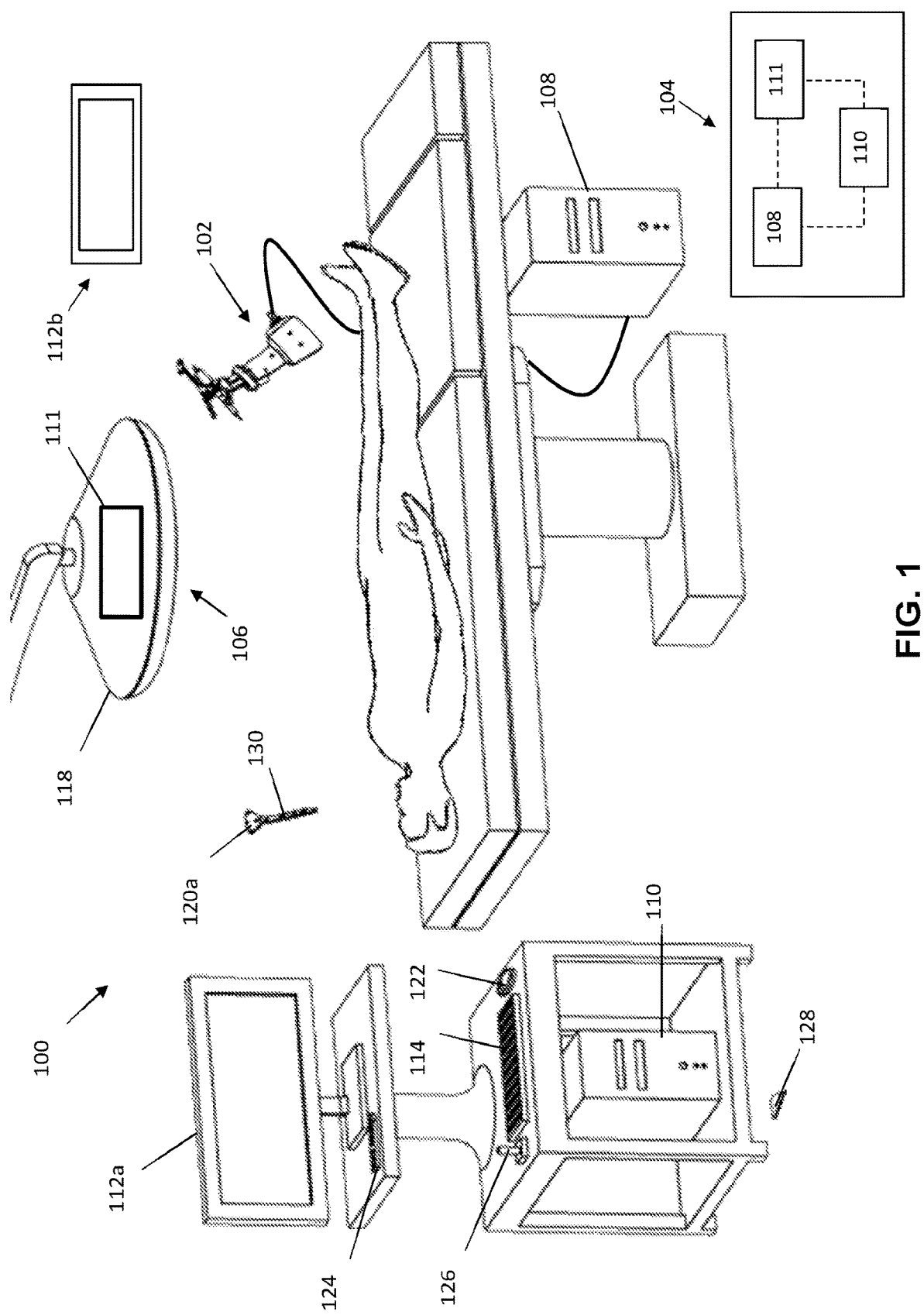
FIG. 1 is a schematic view showing a computer-assisted medical system comprising a two-degree-of-freedom articulating hand-held device.

The present invention comprises the provision and use of a new and improved system and method for accurate alignment of a tool with an axis to perform a medical procedure. For example, aligning a tool with an axis may be particularly useful for creating tunnels in bone for use in ligament and/or tendon reconstruction surgery. The present invention may be used to accurately drill tunnels in bone for use in ligament and/or tendon reconstruction surgery so as to improve clinical outcomes. The present invention will now be described with reference to the following embodiments. As is apparent by the following description, and as will be appreciated by those skilled in the art, the present invention can be embodied in different forms and should not be construed as limited to the embodiments set forth herein. By way of example but not limitation, features illustrated with respect to one embodiment of the present invention can be incorporated into other embodiments of the present invention, and features illustrated with respect to a particular embodiment of the present invention may be omitted from that embodiment (or other embodiments) of the present invention. In addition, numerous variations and additions to the embodiments of the present invention suggested herein will be apparent to those skilled in the art in light of the instant disclosure. Hence, the following description is intended to illustrate some exemplary preferred embodiments of the invention, and not to exhaustively specify all permutations, combinations, and variations thereof.

Furthermore, it should also be appreciated that although the systems and methods described herein provide examples with reference to anterior cruciate ligament (ACL) reconstruction procedures, the systems and methods of the present invention may be applied to other computer-assisted medical procedures involving other tissues in the body, both hard and soft tissues alike. By way of example but not limitation, the system and method of the present invention may be applied to medical procedures performed on: a) hard tissues (e.g., bones, teeth) including bones in the hip, ankle, shoulder, spine, jaw, skull, elbow, wrist, hands, fingers, feet, toes, etc., as well as revision of initial repair or replacement of any joints or bones; and b) soft tissues (e.g., organs, muscles, connective tissue) including the brain, ligaments, tendons, lungs, heart, skin, etc. Examples of other medical procedures that may be performed with the system and methods described herein illustratively include total and partial joint replacement; unicompartmental arthroplasty; bone fracture repair; osteotomies; spinal reconstruction and pedicle screw placement; biopsies; radiation, laser, carbon dioxide, radiofrequency, or ablation treatments; and the like.

As used herein, the term "pre-procedure data" refers to data used to plan a medical procedure prior to making modifications to the tissue. The pre-procedure data may include one or more of the following: an image data set of tissue (e.g., an image data set acquired via computed tomography (CT), magnetic resonance imaging (MRI), ultrasound, x-ray, laser scan, etc.), a virtual generic model of the tissue, a physical model of the tissue, a virtual patient-specific model of the tissue generated from an image data set of the tissue, a set of data collected directly on the tissue intraoperatively (commonly used with imageless computer-assist devices), etc.

As used herein, the term "digitizer" refers to a device capable of measuring, collecting, or designating the location of physical points or tissue structures in three-dimensional space. By way of example but not limitation, the "digitizer" may be: a "mechanical digitizer" having passive links and joints, such as the high-resolution electro-mechanical sensor arm described in U.S. Pat. No. 6,033,415 (which U.S. patent is hereby incorporated herein by reference); a non-mechanically tracked digitizer probe (e.g., optically tracked, electromagnetically tracked, acoustically tracked, and equivalents thereof) as described for example in U.S. Pat. No. 7,043,961 (which U.S. patent is hereby incorporated herein by reference); an end-effector of a robotic device; or a laser scanner.

As used herein, the term "digitizing" refers to collecting, measuring, and/or recording the location of physical points or tissue structures in space using a digitizer.

As used herein, the term "registration" refers to the determination of the spatial relationship between two or more objects, and/or the determining of a coordinate transformation between two or more coordinate systems associated with those objects. Examples of objects routinely registered to one another in an operating room (OR) illustratively include: computer-assisted medical systems/devices; tissue structures (e.g., a bone); pre-procedure data (e.g., 3-D virtual tissue models); medical planning data (e.g., position of a targeted axis relative to tissue; position of virtual planes relative to a targeted axis; other axes, planes, or boundaries; an implant or tunnel model; a computer software "cut-file" having cutting parameters such as cutting parameters, cutting paths, velocities, feed rates, etc.; or any other planned geometries or objects associated with or defined relative to pre-procedure data); and any external landmarks (e.g., a tracking array affixed to tissue, an anatomical landmark, a designated point/feature on a bone, etc.) associated with the tissue (if such landmarks exist). Various methods of registration are well known in the art and are described in, for example, U.S. Pat. Nos. 6,033,415, 8,010,177, and 8,287,522, which patents are hereby incorporated herein by reference.

As used herein, the term "real-time" refers to the processing of input data within milliseconds, such that calculated values are available within 2 seconds of computational initiation.

As used herein, the term "optical communication" refers to wireless data transferred via modulated infrared or visible light as described in U.S. Patent Application Publication No. 2017/0245945 assigned to the assignee of the present application and incorporated by reference herein in its entirety.

As used herein, the terms "computer-assisted medical systems" or "computer-assisted medical devices" refer to any system or device requiring a computer to aid in a medical procedure. Examples of computer-assisted medical systems or devices include a tracking system, tracked passive instruments, active or semi-active articulated hand-held devices and associated systems, automated or semi-automated serial-chain manipulator systems, haptic serial chain manipulator systems, parallel robotic systems, or master-slave robotic systems, as described in U.S. Pat. Nos. 5,086,401; 7,206,626; 8,876,830; and 8,961,536; and U.S. Patent Application Publication No. 2013/0060278, which patents and patent application are incorporated herein by reference. A particular computer-assisted medical system equipped to execute embodiments of the inventive method described herein comprises a two-degree-of-freedom articulating hand-held device (referred to herein as a 2-DoF device) as described in U.S. patent application Ser. No. 15/778,811 (published as U.S. Patent Application Publication No. 2018/0344409) assigned to the assignee of the present application and incorporated by reference herein in its entirety. A 2-DoF device may include a working portion and a hand held portion, where the working portion is actuated in two-degrees-of-freedom relative to the hand-held portion as further described below with reference to FIGS. 1, 2A and 2B. It should be appreciated that other articulating hand-held devices with greater than two-degrees-of-freedom may be utilized, especially if one or more of the additional degrees-of-freedom is locked such that the hand-held device operates in two-degrees-of-freedom.

As used herein, the term "reference marker" refers to an implement that acts a point of reference for a user, a guide, or a computer-assisted medical device to assist with aligning a tool with an axis. A reference marker may be fixed, attached, adhered, connected, or otherwise affixed to an anatomical region. The anatomical region may include hard or soft tissue, but should be sufficiently rigid such when two or more reference markers are assembled to the anatomical region, the reference markers can maintain their position and relative relationship. Examples of a reference marker include a pin, a tack, a screw, a nail, an adhesive marker, or any other structure to act as a point of reference to assist in aligning a tool with an axis.

As used herein, the term "tool" refers to an instrument that affects, contacts, does work on, or applies energy, medication or other components to tissue. Examples of a tool include at least one of a pin, a screw, a drill bit, a reference marker, a reamer, a mill, a cutter, a saw, a probe, a tissue remover, forceps, a needle, a laser (e.g., focused electromagnetic radiation, carbon-dioxide), a radio-frequency emitter, an ablation instrument, a water-jet, a cannula, etc.

With reference now to the Figures, and in particular FIGS. 1, 2A, and 2B, embodiments of the present inventive system and method generally comprises a computer-assisted medical system comprising a 2-DoF device 102 to assist in aligning a tool with an axis. FIG. 1 is a schematic view showing the computer-assisted medical system 100 comprising a 2-DoF device 102, a computing system 104, and a tracking system 106.

FIGS. 2A and 2B are schematic views showing the 2-DoF device 102 in greater detail. More particularly, FIG. 2A shows the 2-DOF device 102 in a first working position and orientation (POSE), and FIG. 2B illustrates the 2-DOF device 102 in a second working POSE. The 2-DoF device 102 comprises a hand-held portion 202 (or handle) and a working portion 204. The hand-held portion 202 comprises an outer casing 203 of ergonomic design which can be held and wielded by a user (e.g., a surgeon). The working portion 204 comprises a coupler 209 for removably connecting a tool 206 having a tool axis 207 to the working portion 204. The tool 206 may be removably coupled to the working portion 204 and driven by a motor 205. The hand-held portion 202 and working portion 204 are connected to one another, for example, by a front linear rail 208a and a back linear rail 208b that are actuated by components in the hand-held portion 202 in order to control the pitch and translation of the working portion 204 relative to the hand-held portion 202, as will hereinafter be discussed in further detail. In a particular embodiment, the working portion 204 is removably connected to the hand-held portion 202 to permit different types of working portions to be assembled to the hand-held portion 202. For example, the working portion 204 may be a laser system having components to operate a laser for treating tissue.

A tracking array 212, having three or more fiducial markers of the sort well known in the art, is preferably rigidly attached to the working portion 204 in order to permit the tracking system 106 (FIG. 1) to track the POSE of the working portion 204. The three or more fiducial markers may, alternatively, be integrated directly with the working portion 204. The fiducial markers may be active markers such as light emitting diodes (LEDs), or passive markers such as retroreflective spheres. The 2-DoF device 102 may further include one or more user input mechanisms such as triggers (e.g., trigger 214) or button(s). The user input mechanisms may permit the user to perform various functions illustratively including: activating or deactivating the motor 205; activating or deactivating the actuation of the working portion 204; notifying the computing system 104 to change from targeting one virtual plane to a subsequent virtual plane; and pausing the medical procedure.

Still looking at FIGS. 2A and 2B, within the outer casing of the hand-held portion 202 are a front actuator 210a that powers a front ball screw 216a, and a back actuator 210b that powers a back ball screw 216b. The actuators (front actuator 210a, back actuator 210b) are preferably servomotors that bi-directionally rotate the ball screws (216a, 216b). A first end of the linear rails (front linear rail 208a, back linear rail 208b) are attached to the working portion 204 via hinges (220a, 220b), such that the hinges (220a, 220b) allow the working portion 204 to pivot relative to the linear rails (208a, 208b). Ball nuts (218a, 218b) are attached at a second end of the linear rails (208a, 208b). The ball nuts (218a, 218b) are in mechanical communication with the ball screws (216a, 216b). The actuators (210a, 210b) power the ball screws (216a, 216b) which in turn cause the ball nuts (218a, 218b) to translate along the axis of the ball screws (216a, 216b). Translation of ball nuts 218a, 218b along ball screws 216a, 216b, respectively, causes translation of front linear rail 208a and back linear rail 208b, respectively, whereby to permit (a) selective linear movement of working portion 204 relative to hand-held portion 202, and (b) selective pivoting of working portion 204 relative to hand-held portion 202 of 2-DoF device 102. Accordingly, the translation "d" and pitch "a" (FIG. 2B) of the working portion 204 may be adjusted depending on the position of each ball nut (218a, 218b) on their corresponding ball screw (216a, 216b). A linear guide 222 (FIG. 2A) may further constrain and guide the motion of the linear rails (208a, 208b) in the translational direction "d".

The 2-DoF device 102 may receive power via an input/output port (e.g., from an external power source) and/or from on-board batteries (not shown).

The actuators (210a, 210b) and/or motor 205 of the 2-DoF device 102 may be controlled using a variety of methods. By way of example but not limitation, according to one method of the present invention, control signals may be provided via an electrical connection to an input/output port. By way of further example but not limitation, according to another method of the present invention, control signals are communicated to the 2-DoF device 102 via a wireless connection, thereby eliminating the need for electrical wiring. If desired, the wireless connection may be made via optical communication. In a preferred embodiment, the 2-DoF device 102 includes a receiver for receiving control signals from the computing system 104 (FIG. 1). The receiver may be, for example, an input port for a wired connection (e.g., Ethernet port, serial port), a transmitter, a modem, a wireless receiver (e.g., Wi-Fi receiver, Bluetooth® receiver, a radiofrequency receiver, an optical receiver (e.g., photosensor, photodiode, camera)), or a combination thereof. The receiver may send control signals from the computing system 104 directly to the actuators (210a, 210b) and/or motor 205 of the 2-DoF device 102, or the receiver may be in communication with a processor (e.g., an on-board device computer 108 as further described below) to pre-process the control signals before sending to the actuators (210a, 210b) and/or motor 205.

Looking again at FIG. 1, the computing system 104 generally includes hardware and software for executing a medical procedure. By way of example but not limitation, in one preferred form of the present invention, the computing system 104 is configured to control the actuation of the working portion 204 relative to the hand-held portion 202 of the 2-DoF 102 device to maintain the tool axis 207 (FIG. 2B) coincident with a virtual plane defined in a medical plan. The computing system 104 accurately maintains the tool axis 207 coincident with a virtual plane defined in the medical plan based on: a) the registered location of the medical plan to the location of the tissue; b) the tracked location of the tissue; and c) the tracked POSE of the 2-DoF device 102.

The computing system 104 of the computer-assisted medical system 100 may include: a device computer 108 (or microcontroller) comprising a processor; a planning computer 110 (or microcontroller) comprising a processor; a tracking computer 111 (or microcontroller) comprising a processor, and peripheral devices. Processors operate in the computing system 104 to perform computations and execute software associated with the inventive system and method. The device computer 108, the planning computer 110, and the tracking computer 111 may be separate entities as shown in FIG. 1, or it is also contemplated that operations may be executed on one (or two) computers or processors depending on the configuration of the computer-assisted medical system 100. For example, the tracking computer 111 may have operational data to control the 2-DoF device 102 without the need for a device computer 108. Alternatively, if desired, the device computer 108 may include operational data to plan the medical procedure without the need for the planning computer 110. Furthermore, if desired, any combination of the device computer 108, planning computer 110, and/or tracking computer 111 may be connected together via a wired or wireless connection. In addition, the data gathered by, and/or the operations performed by, the tracking computer 111 and device computer 108 may work together to control the 2-DoF device 102 and, as such, the data gathered by, and/or the operations performed by, the tracking computer 111 and device computer 108 to control the 2-DoF device 102 may be referred to herein as a "control system".

The peripheral devices allow a user to interface with the computing system 104 and may include, but are not limited to, one or more of the following: one or more user-interfaces, such as a display or monitor (112a, 112b) to display a graphical user interface (GUI); and user-input mechanisms, such as a keyboard 114, mouse 122, pendent 124, joystick 126, and foot pedal 128. If desired, the monitor(s) (112a, 112b) may have touchscreen capabilities, and/or the 2-DoF device 102 may include one or more input mechanisms (e.g., buttons, switches, etc.). Another peripheral device may include a tracked digitizer probe 130 to assist in the registration process. A tracking array 120a is assembled to the digitizer probe 130 to permit the tracking system 106 to track the POSE of the digitizer probe 130 in space. The digitizer probe 130 may further include one or more user input mechanisms to provide input to the computing system 104. For example, a button on the digitizer probe 130 may allow the user to signal to the computing system 104 to collect or record a point in space to assist in registering a tissue structure to a medical plan.

The device computer 108 may include one or more processors, controllers, software, data, utilities, and/or storage medium(s) such as RAM, ROM or other non-volatile or volatile memory to perform functions related to the operation of the 2-DoF device 102. By way of example but not limitation, the device computer 108 may include software, data, and utilities to control the 2-DoF device 102, e.g., such as to control the POSE of the working portion 204, receive and process tracking data, control the speed of the motor 205, execute registration algorithms, execute calibration routines, provide workflow instructions to the user throughout a medical procedure, as well as any other suitable software, data or utilities required to successfully perform the procedure in accordance with embodiments of the invention. The device computer 108 may be located separate from the 2-DoF device 102 as shown in FIG. 1, or the device computer 108 may be housed in the hand-held portion 202 of the 2-DoF device 102 to provide on-board control. If the device computer 108 is housed in the hand-held portion 202, referred to hereinafter as on-board device computer, the on-board device computer may receive external data (e.g., tracking data, informational data, workflow data, etc.) via a wired or wireless connection. Similarly, an on-board device computer may send internal data (e.g., operational data, actuator/ball-screw position data, battery life, etc.) via a wired or wireless connection. In a preferred embodiment, external data may be received and/or internal data is sent wirelessly using optical communications. Details about bi-directional optical communication between a 2-DoF device 102 and a tracking system 106 is further described below.

The planning computer 110 is preferably dedicated to planning the procedure. By way of example but not limitation, the planning computer 110 may contain hardware (e.g., processors, controllers, memory, etc.), planning software, data, and/or utilities capable of: receiving, reading, and/or manipulating medical imaging data; segmenting imaging data; constructing and manipulating three-dimensional (3D) virtual models; storing and providing computer-aided design (CAD) files such as bone pin CAD files; planning the POSE of axes (e.g., a targeted axis, an axis for laser treatment, an axis that reaches a cancerous tissue location), planes, screws, pins, implants, alignment guides, bone tunnels, and/or 3-D virtual ligament or tendon grafts relative to pre-procedure data; generating the medical planning data for use with the system 100, and providing other various functions to aid a user in planning the medical procedure. The planning computer also contains software dedicated to defining virtual planes with regards to embodiments of the invention as further described below. The final medical plan data may include an image data set or virtual model of the tissue, tissue registration data, subject identification information, the POSE of one or more pins, screws, implants, or bone tunnels relative to the tissue, and/or the POSE of one or more axes and virtual planes defined relative to the tissue. The device computer 108 and the planning computer 110 may be directly connected in the procedure room, or may exist as separate entities outside the procedure room. The final medical plan is readily transferred to the device computer 108 and/or tracking computer 111 through a wired (e.g., electrical connection) or a wireless connection (e.g., optical communication) in the procedure room; or transferred via a non-transient data storage medium (e.g., a compact disc (CD), or a portable universal serial bus (USB drive)) if the planning computer 110 is located outside the procedure room (or if otherwise desired). As described above, the computing system 104 may comprise one or more computers or microcontrollers, with multiple processors capable of performing the functions of the device computer 108, the tracking computer 111, the planning computer 110, or any combination thereof.

The tracking system 106 (FIG. 1) of the present invention generally includes a detection device to determine the POSE of an object relative to the position of the detection device. In particular embodiments of the present invention, the tracking system 106 is an optical tracking system such as the optical tracking system described in U.S. Pat. No. 6,061,644 (which patent is hereby incorporated herein by reference), having two or more optical detectors (e.g., cameras) for detecting the position of fiducial markers 121 (FIG. 4) arranged on rigid bodies or integrated directly on the tracked object. By way of example but not limitation, the fiducial markers 121 may comprise: an active transmitter, such as an LED or electromagnetic radiation emitter; a passive reflector, such as a plastic sphere with a retro-reflective film; or a distinct pattern or sequence of shapes, lines or other characters. A set of fiducial markers 121 arranged on a rigid body, or integrated on a device, is sometimes referred to herein as a tracking array, wherein each tracking array comprises a unique geometry/arrangement of fiducial markers 121, or a unique transmitting wavelength/frequency (if the markers are active LEDS), such that the tracking system 106 can distinguish between each of the tracked objects.

If desired, the tracking system 106 may be incorporated into a procedure room light 118 (FIG. 1), located on a boom, a stand, or built into the walls or ceilings of the procedure room. The tracking system computer 111 includes tracking hardware, software, data, and/or utilities to determine the POSE of objects (e.g., tissue structures, the 2-DoF device 102) in a local or global coordinate frame. The output from the tracking system 106 (i.e., the POSE of the objects in 3-D space) is referred to herein as tracking data, where this tracking data may be readily communicated to the device computer 108 through a wired or wireless connection. In a specific embodiment, the tracking computer 106 processes the tracking data and provides control signals directly to the 2-DoF device 102 and/or device computer 108 based on the processed tracking data to control the position of the working portion 204 of the 2-DoF device 102 relative to the hand-held portion 202.

The tracking data is preferably determined using the position of the fiducial markers detected from the optical detectors and operations/processes such as image processing, image filtering, triangulation algorithms, geometric relationship processing, registration algorithms, calibration algorithms, and coordinate transformation processing.

Bi-directional optical communication (e.g., light fidelity or Li-Fi) may occur between the 2-DoF device 102 and the tracking system 106 by way of a modulated light source (e.g., light emitting diode (LED)) and a photosensor (e.g., photodiode, camera). The 2-DoF device 102 may include an LED and a photosensor (i.e., a receiver) disposed on the working portion 204 or hand-held portion 202, where the LED and photosensor are in communication with a processor such as modem or an on-board device computer. Data generated internally by the 2-DoF device 102 may be sent to the tracking system 106 by modulating the LED, where the light signals (e.g., infrared, visible light) created by the modulation of the LED are detected by the tracking system optical detectors (e.g., cameras) or a dedicated photosensor and processed by the tracking system computer 111. The tracking system 106 may likewise send data to the 2-DoF device 102 with a modulated LED associated with the tracking system 106. Data generated by the tracking system 106 may be sent to the 2-DoF device 102 by modulating the LED on the tracking system 106, where the light signals are detected by the photosensor on the 2-DoF device 102 and processed by a processor in the 2-DoF device 102. Examples of data sent from the tracking system 106 to the 2-DoF device 102 includes operational data, medical planning data, informational data, control data, positional or tracking data, pre-procedure data, or instructional data. Examples of data sent from the 2-DoF device 102 to the tracking system 106 may include motor position data, battery life, operating status, logged data, operating parameters, warnings, or faults.

It should be appreciated that in some embodiments of the present invention, other tracking systems are incorporated with the medical system 100. By way of example but not limitation, the medical system 100 may comprise an electromagnetic field tracking system, ultrasound tracking systems, accelerometers and gyroscopes, and/or a mechanical tracking system. The replacement of a non-mechanical tracking system with other tracking systems will be apparent to one skilled in the art in view of the present disclosure. In one form of the present invention, the use of a mechanical tracking system may be advantageous depending on the type of medical system used such as the computer-assisted surgical system described in U.S. Pat. No. 6,322,567 assigned to the assignee of the present application and incorporated herein by reference in its entirety.

Aligning a Tool With an Axis Using a 2-DoF Device

Figure 3A:
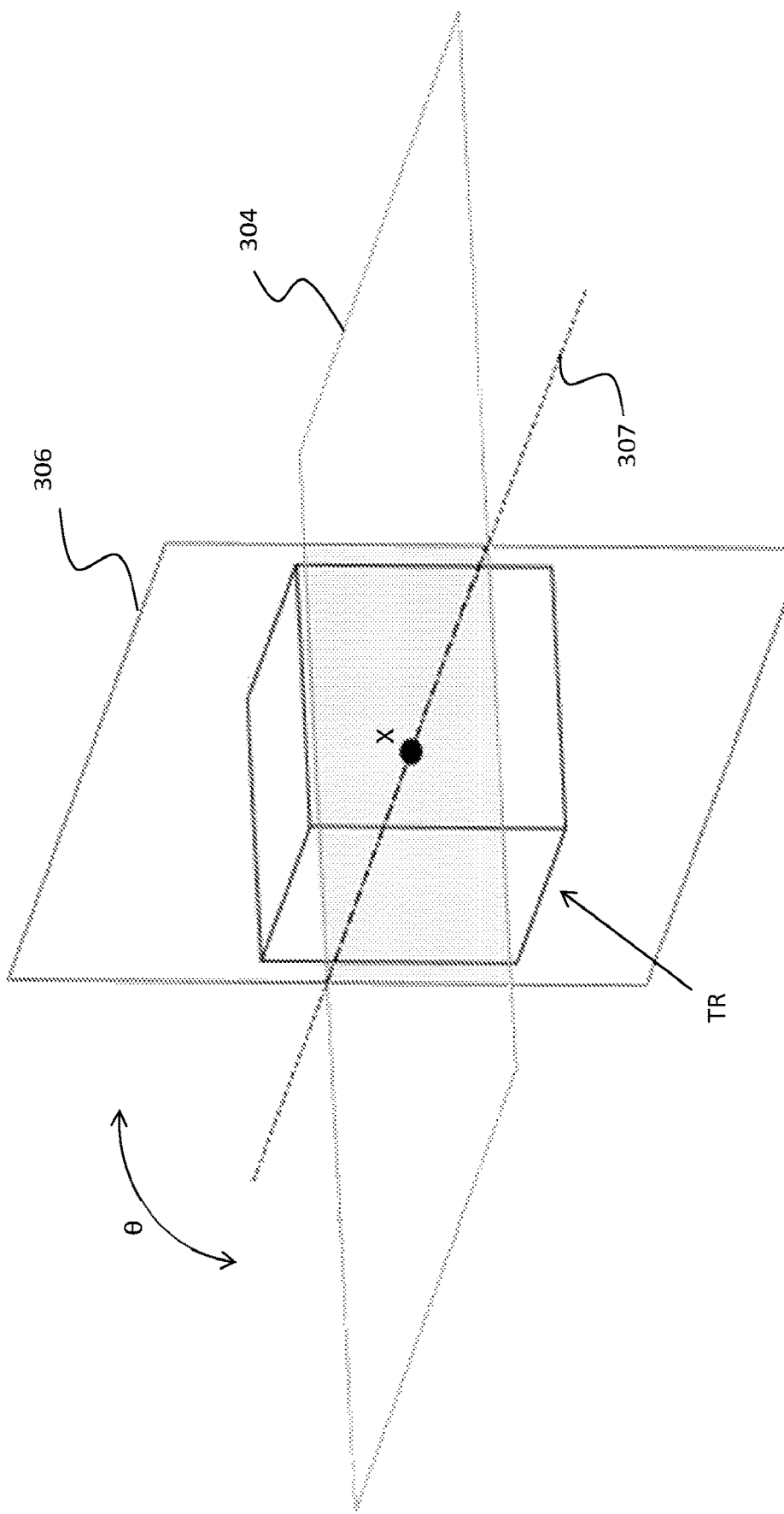
FIG. 3A is a schematic view showing a virtual representation of a tissue structure with a planned position for a targeted axis and two intersecting planes defined relative to the targeted axis.

A medical procedure to align a tool with an axis to perform a medical procedure may begin with medical procedure planning. By way of example but not limitation, a medical plan may be generated using planning software. Pre-procedure data is typically acquired and/or generated from medical image data derived from, for example, computed tomography (CT), magnetic resonance imaging (MRI), ultrasound, X-ray, or fluoroscopy. Virtual tissue models may be generated from the medical image data in the planning software using techniques known in the art (e.g., segmentation, marching cubes). FIG. 3A is a schematic view illustrating a tissue representation 'TR', where the representation may be in the form of an image data set or a 3-D model of the tissue. The planning software may include various tools or widgets to allow a user to designate a desired position for a targeted axis 307 relative to the tissue representation 'TR'. The user may further designate one or more specific target locations 'X' along a targeted axis 307. By way of example but not limitation, such tools or widgets may include: virtual tunnel models, virtual tool models, or virtual implants, which may be manipulatable by scale, dimension, or geometry; virtual axes or points; splines or lines; a drawing toolbox to define the dimensions and position for a targeted axis, virtual planes, points, lines, implants, pins, screws, needles, bone tunnels, or implants; virtual ligaments or tendons having mechanical properties representative of native ligaments or tendons; or combinations thereof. If the user only designates a specific target location 'X', the planning software may automatically define a targeted axis 307 to permit a 2-DoF device 102 to reach the specific target location 'X' along the targeted axis 307. The user may alternatively define a targeted axis 307 to reach the specific target location 'X'. The planning software may further include simulation functions to simulate a medical procedure and/or to simulate tissue functions. For example, a range-of-motion between two or more virtual bone models may be simulated.

After the location of a targeted axis 307 is defined relative to the tissue representation 'TR', the planning software is used to manually or automatically define a first virtual plane 304 and a second virtual plane 306 relative to the targeted axis 307. The virtual planes (304, 306) are the alignment targets for the 2-DoF device 102 during the procedure, where the position of the working portion 204 of the 2-DoF device 102 is adjusted relative to the hand-held portion 202 to maintain a tool coupled to the working portion 204 to be coincident with one virtual plane at a time. By way of example but not limitation, FIG. 3A is a schematic view illustrating a perspective view of a tissue representation 'TR' having a first virtual plane 304 and a second virtual plane 306 defined relative to the targeted axis 307. The first virtual plane 304 and second virtual plane 306 may be defined using several methods. By way of example but not limitation, the first virtual plane 304 may be defined using at least one of: the targeted axis 307 and one additional point; or a point along the targeted axis 307 and two additional points. The one or two additional points may be defined by the user or the one or two additional points may be automatically assigned by the planning software. The user may define the one or two additional points relative to the tissue representation 'TR' based on the expected exposure of the tissue during the procedure. The one or two additional points may be anatomical landmarks defined by the user or by the planning software. The planning software may further define the first virtual plane 304 and/or the additional points using historical patient case data from previous medical procedures of the same type. FIG. 3A further illustrates a second virtual plane 306 defined relative to the tissue representation 'TR' and intersecting with the first virtual plane 304, where the intersection axis of the first virtual plane 304 and second virtual plane 306 is coincident with the targeted axis 307. The first virtual plane 304 and the second virtual plane 306 are non-parallel and angularly offset by an angle 'θ' about the targeted axis 307. The angle 'θ' between the first virtual plane 304 and the second virtual plane 306 may be between 10 degrees and 170 degrees, while in other embodiments the angle is between 45 degrees and 135 degrees, while in a further embodiment, the first virtual plane 304 is perpendicular (i.e., 90 degrees) to the second virtual plane 306 as shown in FIG. 3A. In a preferred embodiment, the angle 'θ' between the first virtual plane 304 and the second virtual plane 306 is between 20 degrees and 70 degrees or 110 degrees and 160 degrees to improve the chances of the tracking array 212 on the 2-DoF device 102 being within the field-of-view of the tracking system 106 when switching from the first virtual plane 304 to the second virtual plane 306. After the two virtual planes (304, 306) and targeted axis 307 are defined relative to the tissue representation 'TR', the medical plan may be saved and/or transferred and/or uploaded to a computer-assisted medical system in the procedure room.

Figure 3B:
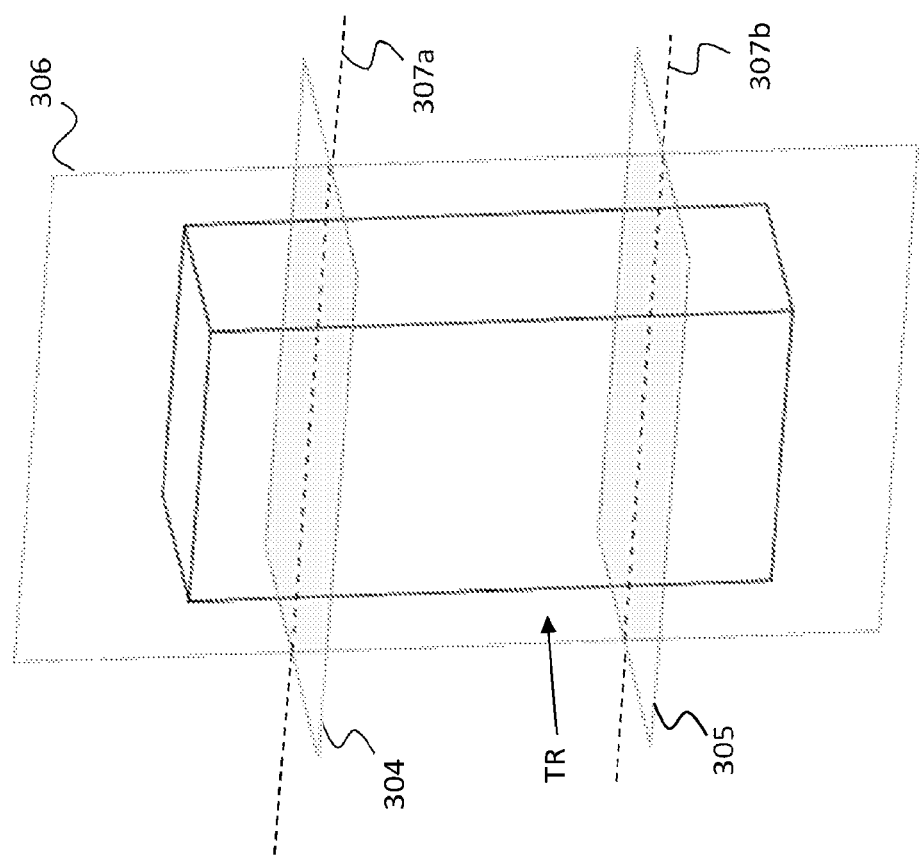
FIG. 3B is a schematic view showing a virtual representation of a tissue structure with a planned position for two targeted axes and three intersecting planes defined relative to the targeted axes.

In a particular embodiment, with reference to FIG. 3B, two or more targeted axes (307a, 307b) may be defined to perform a medical procedure on multiple tissue areas. For example, two targeted axes (307a, 307b) may be defined in the planning software, where a tool can be aligned with a first axis and then with a second axis where the first and second axis may or may not intersect. The first axis may be targeted using two intersecting planes, where one of those planes plus a third plane may be used to target the second axis. For example, FIG. 3B shows two targeted axes (307a and 307b), where three planes (304, 305, and 306) can be defined to permit the 2-DoF device 102 to align a tool with each targeted axis (307a or 307b) independently. The first targeted axis 307a may be targeted using planes 304 and 306, and the second targeted axis 307b may be targeted using planes 305 and 306. This may be extrapolated as having 'n' planes to align a tool with 'n-1' targeted axes. If three planes all intersect in a triangular form, then three axes may be targeted. In addition, a pair of intersecting planes may be defined for two or more targeted axes, where non-intersecting pairs of intersecting planes are defined for each targeted axis. Alternatively, two pairs of intersecting planes may intersect to target four axes.

Figure 4:
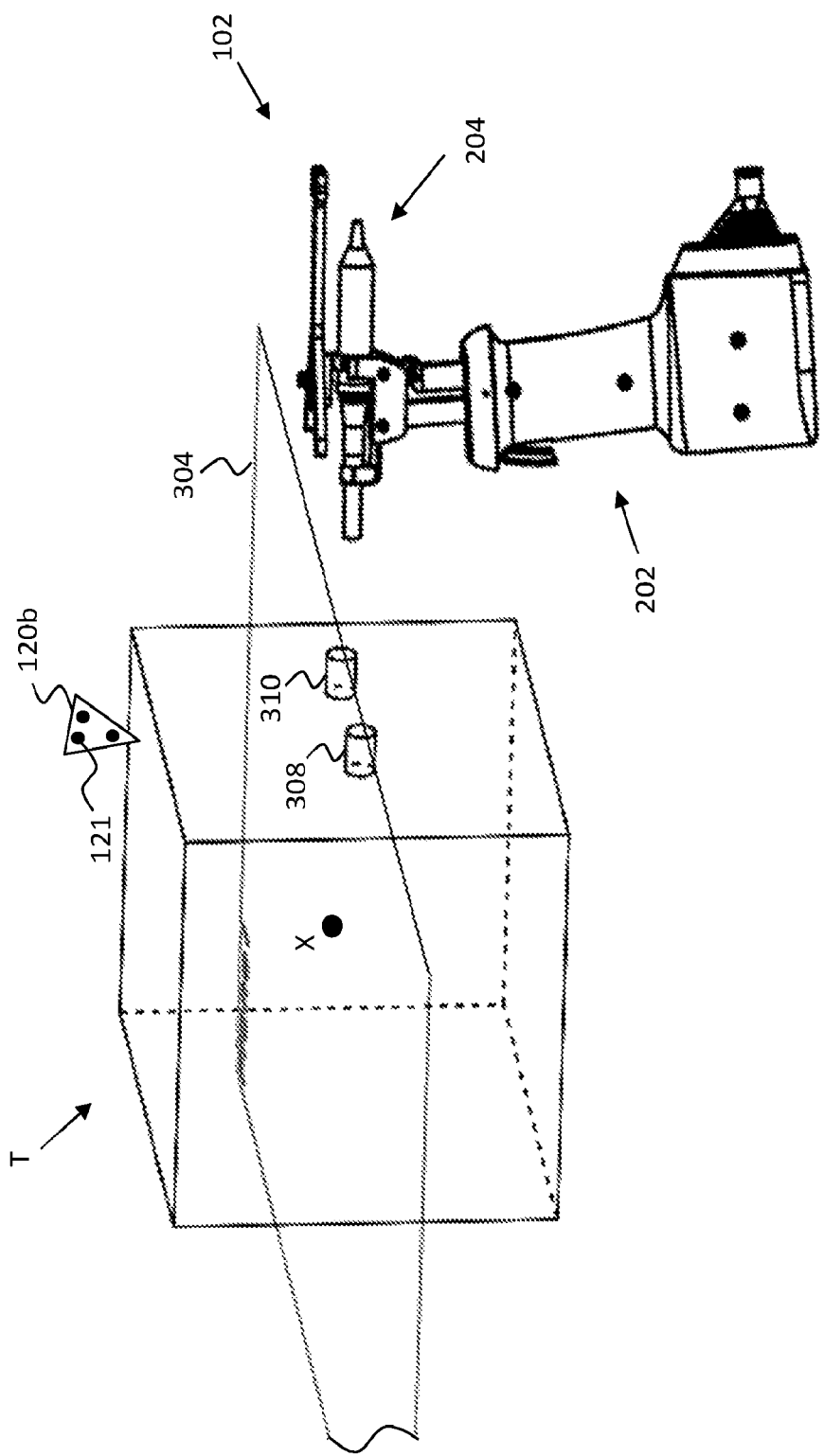
FIG. 4 is a schematic view showing a hand-held device used to place a pair of reference markers into a tissue structure coincident with a first plane.
Figure 5:
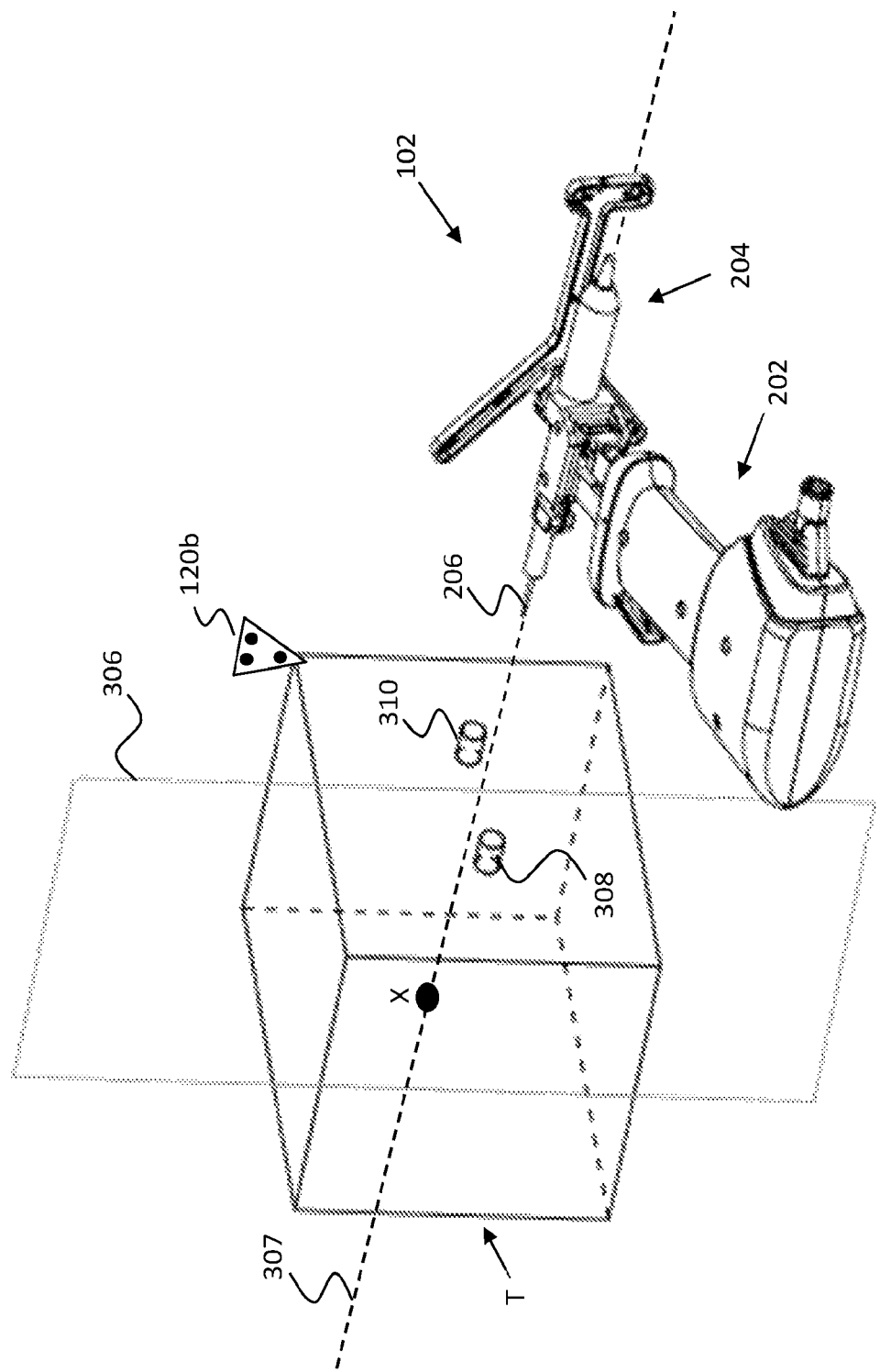
FIG. 5 is a schematic view showing a hand-held device aligned with a targeted axis, where the alignment is accomplished with the use of a pair of reference markers and a second plane.

Looking now at FIGS. 4 and 5, the 2-DoF device 102 is shown executing the medical plan on tissue 'T', where the tissue 'T' corresponds to the same tissue in the tissue representation 'TR' shown in FIG. 3A. A tracking array 120b is fixed to the tissue 'T', and the medical plan is registered to the tissue 'T' using registration techniques known in the art.

After the medical plan is registered to the tissue 'T', and looking now at FIG. 4, a first reference marker 308 is coupled to the hand-held 2-DoF device 102 to be affixed to the tissue 'T' at a location coincident with the first virtual plane 304. In order to affix the first reference marker 308 to the tissue 'T', the 2-DoF device 102 is moved toward and around the patient by the user, and a control system actuates the working portion 204 of the 2-DoF device 102 relative to the hand-held portion 202 to align the reference marker 308 with the first virtual plane 304 (e.g., the user holds the 2-DoF device 102 adjacent to the tissue 'T' with the reference marker 308 coupled to the working portion 204, and the control system provides control signals to the actuators (210a, 210b) to adjust the position of the working portion 204 relative to the hand-held portion 202 to align the reference marker 308 coincident with the first virtual plane 304). The working portion 204 of the 2-DoF device 102 may be automatically actuated (e.g., whenever the 2-DoF device 102 is in the field-of-view of the tracking system 106), or the user may activate/deactivate the actuation by way of an input mechanism such as a trigger, button, or foot pedal. Once the first reference marker 308 is aligned, the user then operates (e.g., activates the motor 205) and advances the 2-DoF device 102 towards the tissue 'T' to affix the first reference marker 308 into the tissue 'T'. A second reference marker 310 is then affixed to the tissue 'T' coincident with the first virtual plane 304 in the same manner as the first reference marker 308, but with the second reference marker 310 being laterally offset along the plane 304 from the first reference marker 308.

Throughout the procedure, a graphical user interface (GUI) may be displayed on a monitor 112b in the procedure room. The GUI may display any of the following to assist with the procedure: a tissue representation 'TR' of the tissue 'T'; a real-time view of the tissue 'T'; virtual planes (304, 306); a targeted axis 307; the real-time POSE of the 2-DoF device 102 using a representation of the 2-DoF device 102 and the tracked POSE of the 2-DoF device 102; the real-time POSE of the tissue 'T' using a tissue representation 'TR' registered to the tissue 'T' and the tracked POSE of the tissue 'T'; the real-time location of a tool 206 relative to the tissue 'T'; or the real-time location of the 2-DoF device 102 or tool 206, the virtual planes (304, 306) or targeted axis 307, and the tissue 'T' using: a) a tissue representation 'TR' registered to the tissue 'T'; b) the virtual planes (304, 306), and the targeted axis 307 registered to the tissue 'T'; c) the tracked POSE of the tissue 'T'; and c) the tracked POSE of the 2-DoF device 102 where a representation or video of the 2-DoF device 102 is used to display on the GUI.

Once the reference markers (308 and 310) are affixed to the tissue 'T', an alignment guide 312 (See FIGS. 8-10) may be assembled to the first reference marker 308 and second reference marker 310 to form a slot 318 between the first reference marker 308 and second reference marker 310. The alignment guide assembled to the markers (308, 310) provides a guide or reference to the orientation of the first virtual plane 304 while the 2-DoF device 102 aligns a tool 206 coincident with the second virtual plane 306 as described below.

After the reference markers (308, 310) are affixed to the tissue 'T', the user may signal to the computing system 102 to change the plane that the 2-DoF device 102 targets from the first virtual plane 304 to the second virtual plane 306. The user may provide this signal to the computing system 102 with an input mechanism such as a trigger, button, or foot pedal. Looking now at FIG. 5, the tool 206 may be aligned with the targeted axis 307 in the following manner. The user moves the 2-DoF device 102 to align the tool 206 in-line with the first reference marker 308 and the second reference marker 310 (with or without the aid of an alignment guide), and the control system actuates the working portion 204 of the 2-DoF device 102 relative to the hand-held portion 202 so as to align the tool 206 coincident with the second virtual plane 306. If an alignment guide 312 is used, the user may move the 2-DoF device 102 such that the tool 206 is aligned in/with the slot 318 formed by the alignment guide 312, and the control system actuates the working portion 204 of the 2-DoF device 102 relative to the hand-held portion 202 so as to align the tool 206 coincident with the second virtual plane 306. The tool 206 is then aligned with the targeted axis 307 when the tool 206 is coincident with the second virtual plane 306 (by way of the actuation of the working portion 204 of the 2-DoF device 102) and the first virtual plane 304 (by way of referencing the first and second reference markers (308, 310) and/or using the slot 318 formed by the alignment guide 312). With the tool 206 aligned with the targeted axis 307, the tool 206 may be used to perform a medical procedure along the targeted tissue axis 207. In particular embodiments, the tool 206 is a third reference marker that is aligned and affixed to the tissue 'T' and coincident with the targeted axis 307 to assist with a medical procedure as described in the tunnel formation example below. Alternatively, the tool 206 is configured to perform a medical procedure directly without the need for a third reference marker.

The aforementioned system and method is advantageous for accurately aligning a tool with an axis to perform a medical procedure. The user is afforded both accuracy and time efficiency to perform the medical procedure. The systems and methods are particularly advantageous for a hand-held device, and more specifically a 2-DoF hand-held device. A hand-held device is easy to maneuver and can quickly be brought into alignment with an axis. In addition, a hand-held device operating in two-degrees-of-freedom with one translational degree-of-freedom and one rotational degree-of-freedom may be especially suited for aligning a tool coincident with a plane, in which the present system and method exploit the use of intersecting planes to further align the tool with an axis. This allows a user to perform a variety of different medical procedures that go beyond the alignment of a tool with a plane only. The use of planes further provides flexibility for the user to place the reference markers in the tissue anywhere coincident with the targeted plane. Therefore, a user can choose the specific location to insert a reference marker in the tissue as long as the reference marker remains coincident with the plane. Specific examples of the inventive system and method provided below.

Example 1

Bone Tunnel Creation with a 2-DoF Device

The following is an example of the inventive system and method for creating tunnels in bone, which may be particularly useful for ligament or tendon reconstruction surgery. In this example, the aforementioned tissue is bone, the tissue representation is a 3-D virtual model of bone, the reference markers are bone pins, a guide clamp is used as an alignment guide, a third reference marker in the form a bone pin is used to assist in the formation of the bone tunnels, and the targeted axis is a central longitudinal axis of a tunnel to be formed in the bone.

Figure 6B:
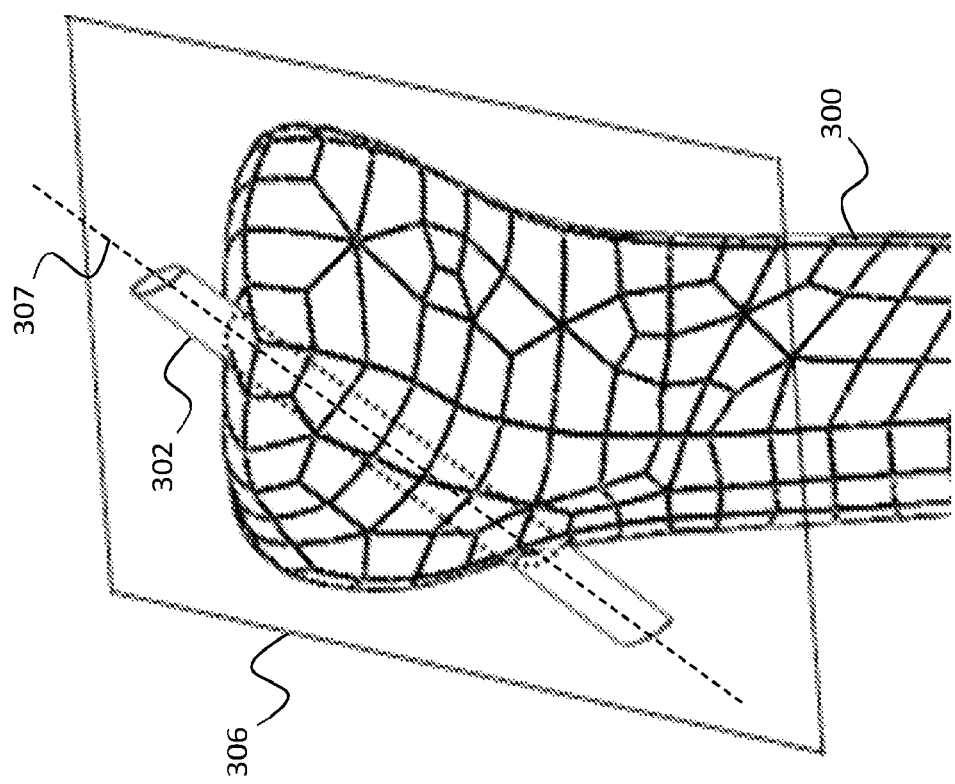
Figure 6A:
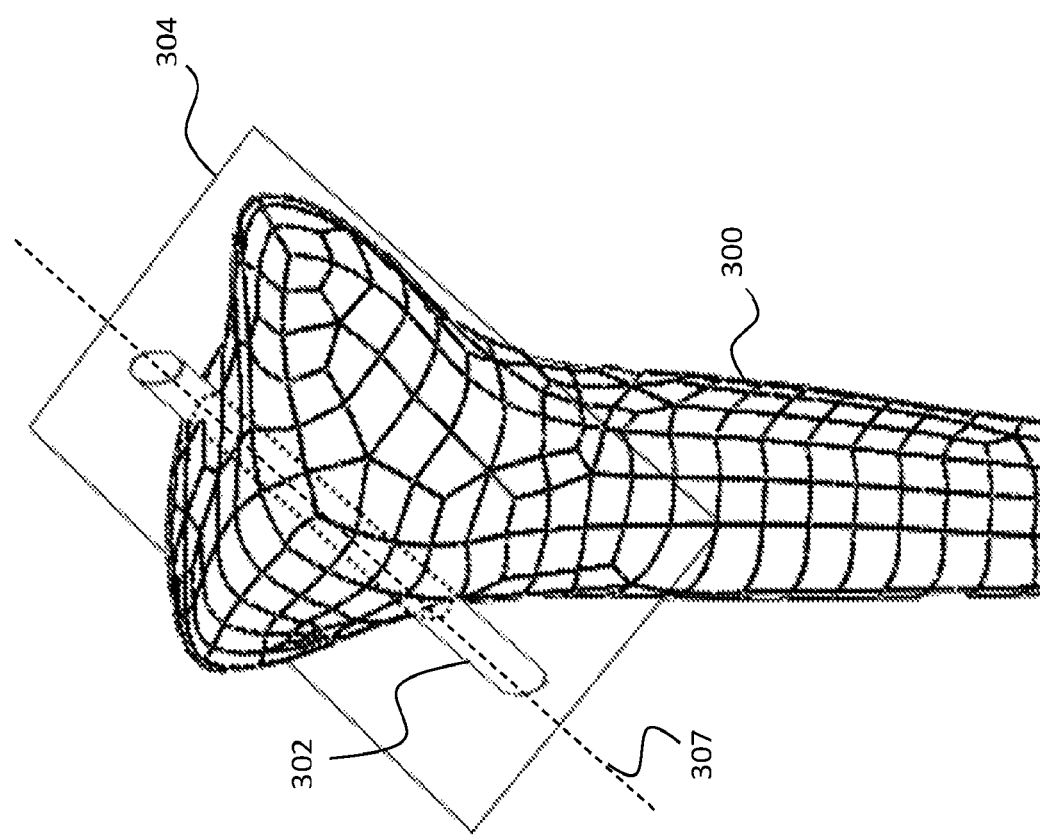

The ligament or tendon reconstruction surgery may begin with pre-operative surgical planning (i.e., medical procedure planning). By way of example but not limitation, a pre-operative surgical plan (i.e., a medical plan) may be generated using planning software. Pre-operative bone data (i.e., pre-procedure data) is typically acquired and/or generated from medical image data derived from, for example, computed tomography (CT), magnetic resonance imaging (MRI), ultrasound, X-ray, or fluoroscopy. Tissue representations in the form of virtual bone models may be generated from the medical image data in the planning software using techniques known in the art (e.g., segmentation, marching cubes). FIGS. 6A and 6B are schematic views illustrating an exemplary tibial bone model 300 generated from a CT scan of the patient's bones. The planning software may include various tools or widgets for allowing a user to designate a desired position for one or more tunnels 302 relative to the tibial bone model 300. By way of example but not limitation, such tools or widgets may include: virtual tunnel model(s), which may be manipulatable by scale, dimension, or geometry; virtual axes or points; splines or lines; a drawing toolbox to define a shape and position for the bone tunnels; virtual ligaments or tendons having mechanical properties representative of native ligaments or tendons; or combinations thereof. The central longitudinal axis 307 (i.e., the targeted axis) of the tunnel 302 may also be displayed to assist with designating a desired position for the tunnel 302. The planning software may further include simulation functions to simulate a range-of-motion between two or more virtual bone models (e.g., motion between a tibial bone model 300 and a femur bone model) with or without a simulation of a tensioning ligament or tendon therebetween.

After the user has designated a desired position for the one or more tunnels 302 relative to the bone models, the planning software may automatically define a first virtual plane 304 and a second virtual plane 306 relative to the one or more tunnel positions. By way of example but not limitation, FIG. 6A is a schematic view illustrating a perspective view of the tibial bone model having a first virtual plane 304 defined relative to the tunnel 302. The first virtual plane 304 may be defined using any of the aforementioned methods. FIG. 6B is a schematic view illustrating a sagittal view of the tibial bone model 300 with a second virtual plane 306 defined relative to the tunnel 302. The first virtual plane 304 and the second virtual plane 306 intersect, and are angularly offset about the intersection axis. The intersection of the first virtual plane 304 and the second virtual plane 306 aligns with the central longitudinal axis 307 of the tunnel. In other words, the intersection axis of the first virtual plane 304 and the second virtual plane 306 is coincident with the central longitudinal axis 307 of the tunnel 302. After the two virtual planes (304, 306) and the position for the tunnel 302 are defined relative to one or more virtual bone models, the surgical plan may be saved and/or transferred to a computer-assisted medical device in an operating room (OR). In a particular embodiment, the planning may occur in the operating room (OR) and is readily available to the computer-assisted medical device without having to transfer or upload the planning data.

Looking now at FIGS. 7-11, the 2-DoF device 102 is shown executing the surgical plan on a tibial bone 'TB'. A tracking array 120b is mounted to the tibial bone 'TB', and the surgical plan is registered to the tibial bone 'TB' using the patient's actual position in the OR and registration techniques known in the art.

Figure 7:
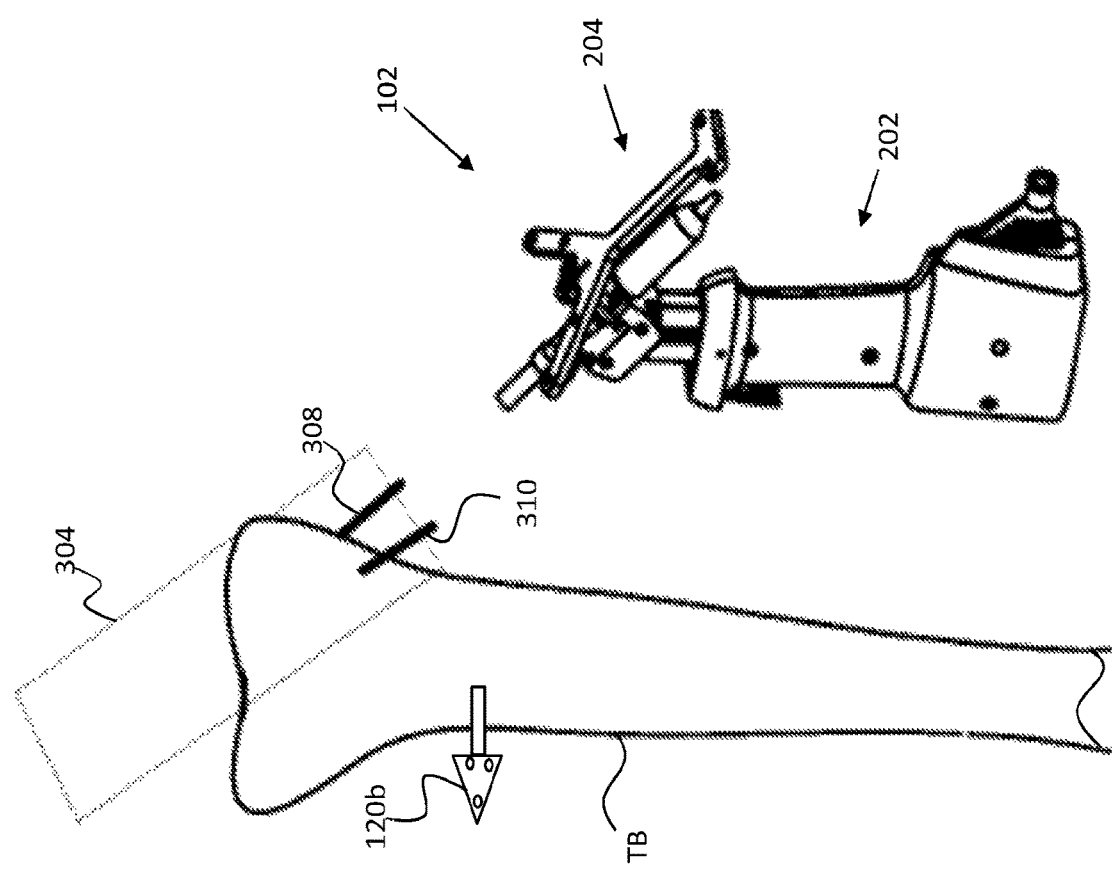
FIG. 7 is a schematic view showing a hand-held device used to insert a first bone pin and a second bone pin into a bone.

After the surgical plan is registered to the tibial bone 'TB', and looking now at FIG. 7, a first removable bone pin 308 (i.e., a first reference marker) is coupled to the hand-held 2-DoF device 102 to be inserted into the tibia bone 'TB' at a location coincident with the first virtual plane 304. In order to affix the first bone pin 308 to the tibia, the hand-held 2-DoF device 102 is moved toward and around the patient by the user, and a control system actuates the working portion 204 of the 2-DoF device 102 relative to the hand-held portion 202 to align the first bone pin 308 coincident with the first virtual plane 304 (e.g., the user holds the 2-DoF device 102 such that the bone pin 308 is adjacent to the tibia bone 'TB', and the control system provides control signals to the actuators (210a, 210b) to adjust the position of the working portion 204 relative to the hand-held portion 202 to align the first bone pin 308 coincident with the first virtual plane 304). Once the first bone pin 308 is aligned, the user then activates the motor 205 and advances the 2-DoF device 102 towards the tibial bone 'TB' to insert the first bone pin 308 into the tibial bone 'TB'. A second removable bone pin 310 (i.e., a second reference marker) is then inserted in the tibial bone 'TB' coincident with the first virtual plane 304 in the same manner as the first removable bone pin 308, but with the second bone pin 310 being laterally offset from the first bone pin 308.

Figure 8:
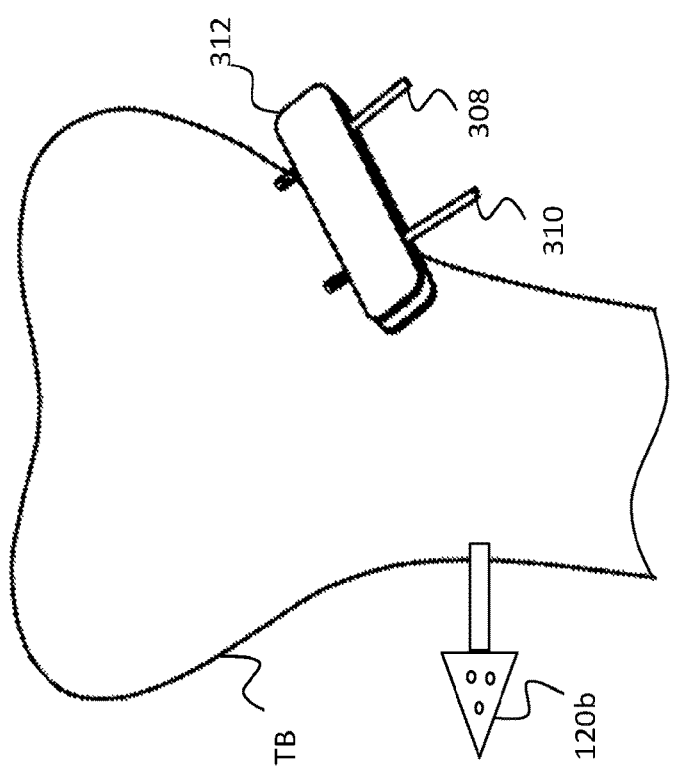
FIG. 8 is a schematic view showing a guide clamp mounted to the first bone pin and the second bone pin.
Figure 9:
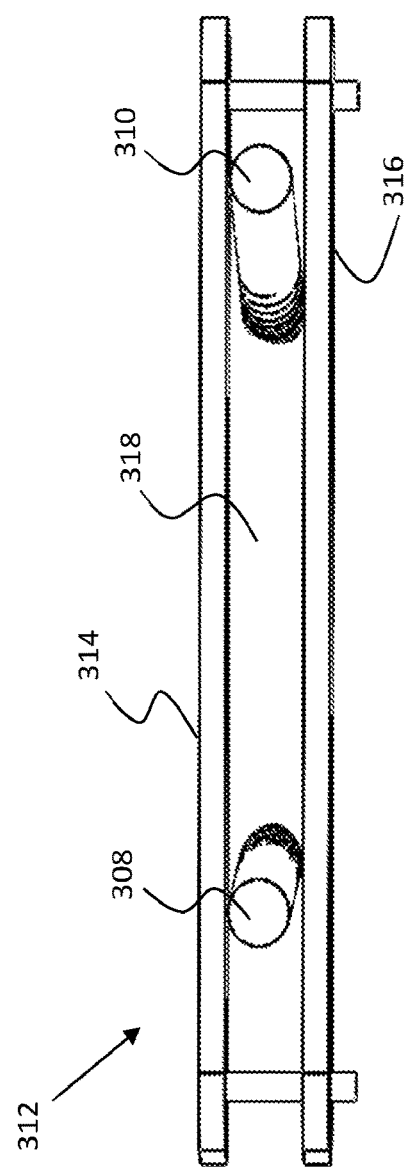
FIG. 9 is a schematic view showing further details of a guide clamp mounted to the first bone pin and the second bone pin.

Looking next at FIG. 8, a guide clamp 312 (i.e., an alignment guide) is then mounted to the first bone pin 308 and second bone pin 310. In one preferred form of the present invention, the guide clamp 312 comprises two parallel plates (314, 316) (or jaws) that clamp down onto the bone pins (308, 310), forming a slot 318 located between the two plates (314, 316) (and between the first bone pin 308 and second bone pin 310) as shown in further detail in FIG. 9

Figure 10:
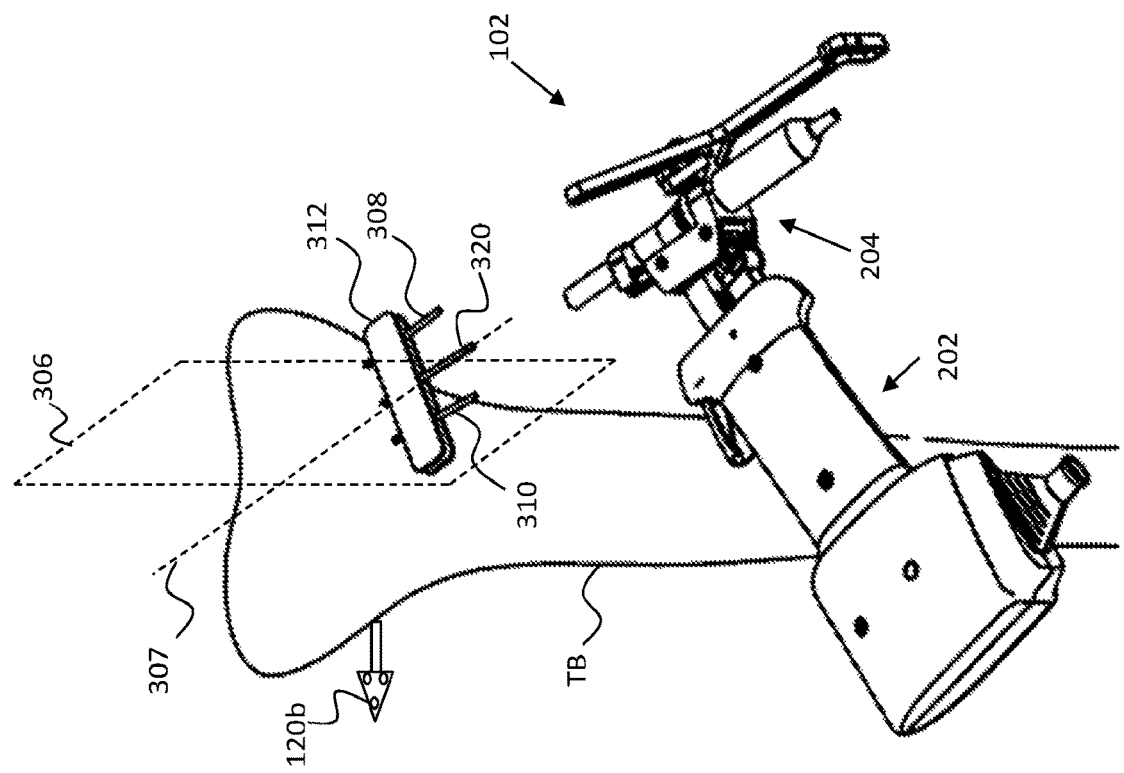
FIG. 10 is a schematic view showing a hand-held device used to insert a third bone pin in a bone through a slot in the guide clamp of FIGS. 8 and 9.

Looking next at FIG. 10, a third bone pin 320 (i.e., a third reference marker) is inserted into the tibial bone 'TB' coincident with the planned position for the central longitudinal axis 307 of the tunnel. The user couples the third bone pin 320 to the working portion 204 of the 2-DoF device 102 and moves the hand-held 2-DoF device 102 toward the patient to insert the third bone pin 320 into the slot 318 formed by the guide clamp 312 and the control system actuates the working portion 204 of the 2-DoF device 102 relative to the hand-held portion 202 so as to align the third bone pin 320 coincident with the second virtual plane 306. Once properly aligned in the slot 318 and coincident with the second virtual plane 306 (and thereby with the planned position for the central longitudinal axis 307 of the tunnel 302), the third bone pin 320 is inserted into the tibial bone 'TB' using the 2-DoF device 102. If desired, the third bone pin 320 may have a smaller diameter than the first bone pin 308 and second bone pin 310 so as to provide enough clearance for the third bone pin 320 to fit in the slot 318 formed by the guide clamp 312. As a result of the procedure discussed above, the longitudinal axis of the third bone pin 320 is now aligned with the central longitudinal axis of the bone tunnel 307 (i.e., the targeted axis) as planned.

Figure 11:
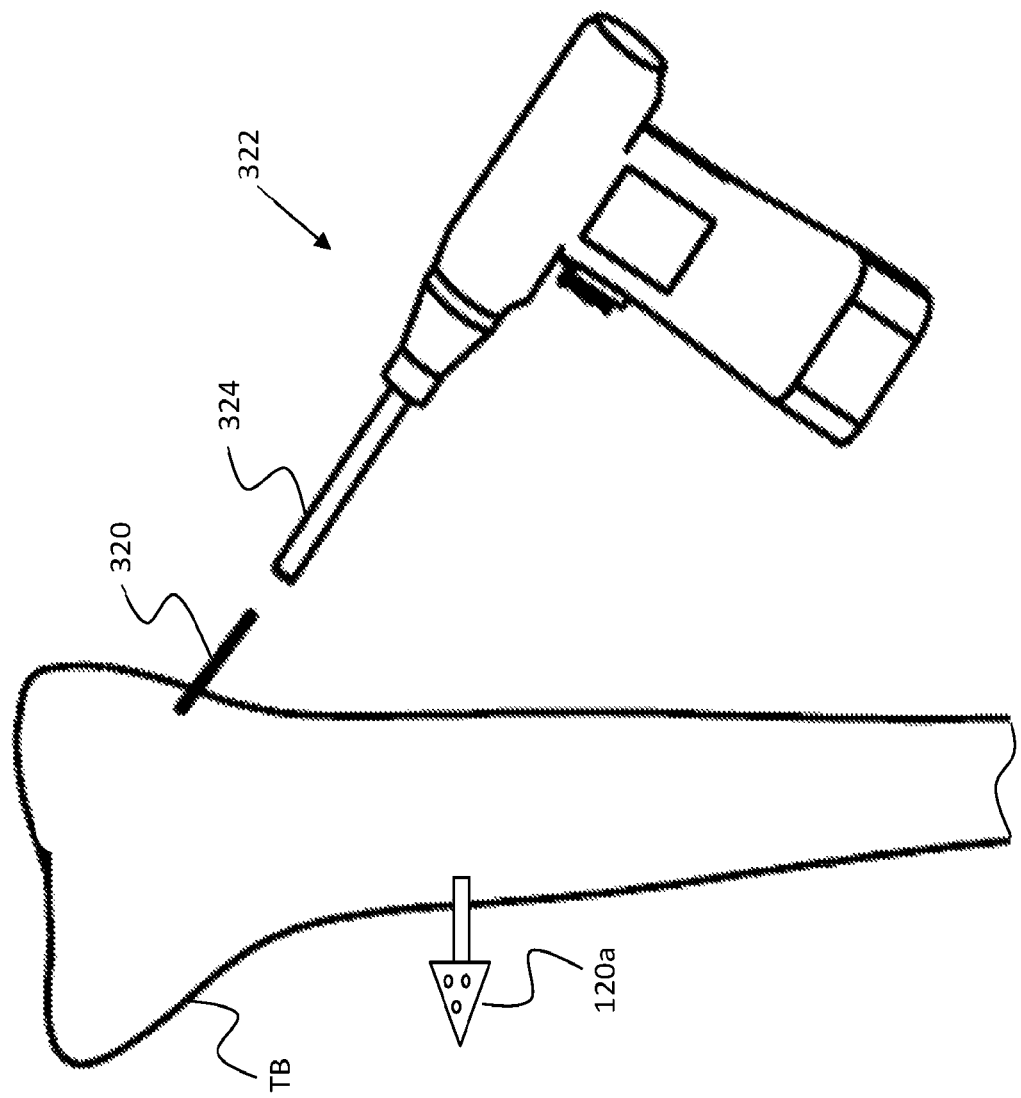
FIG. 11 is a schematic view showing a surgical dill which may be used to create a bone tunnel using a bone pin as a guide.

After the third bone pin 320 has been inserted into the tibial bone T using the 2-DoF device 102, a tunnel may be formed in the bone using the third bone pin 320 as a guide. The guide clamp 312, first bone pin 308, and second bone pin 310 may be removed from the tibial bone T, leaving only the third bone pin 320 in the tibial bone T as shown in FIG. 11. Alternatively, the guide clamp 312, first bone pin 308, and second bone pin 310 may remain on the bone during the formation of the tunnel. In order to form the tunnel a surgical drill 322 operating a hollow drill bit 324 uses the third bone pin 320 as a guide to drill the tunnel. The hollow drill bit 324 slides onto or over the third bone pin 320 and the user drills the tunnel into the bone. Upon retracting the hollow drill bit 324, the third bone pin 320 (and any other components) may be removed in the process.

In a specific embodiment, the tunnel may be formed without the use of a third bone pin 320. After the guide clamp 312 is assembled to the first bone pin 308 and the second bone pin 310, a tool 206 coupled to the 2-DoF device 102 may be used to directly drill the tunnel into the bone. A tool 206, such as a drill bit or other bone removing instrument, may be coupled to the 2-DoF device 102 and once the tool 206 is coincident with the first virtual plane 304 (using the guide slot 318) and the second virtual plane 306 (by way of the actuation of the working portion 204 of the 2-DoF device 102), thereby aligning the tool 206 with the central longitudinal axis 307 of the tunnel, the user may directly drill the tunnel in the bone with the tool 206.

The above procedure may be repeated for a second bone (e.g., a femur bone). In ACL procedures, a first tunnel is created in the tibial bone 'TB', and a second tunnel is created in a femoral bone. After the two tunnels are created, the user can insert a replacement (i.e., graft) ligament into the two tunnels (i.e., the first bone tunnel formed in the tibial bone 'TB' and the second bone tunnel formed in the femoral bone), and the graft ligament is then secured to the bone in ways well known in the art (e.g., by anchors, cross-pins, etc.) to finish the ACL reconstruction procedure.

Example 2

Brain Biopsy With 2-DoF Device

The following is an example of the inventive system and method for retrieving tissue for a biopsy, which may be particularly useful for brain biopsies, bone biopsies, and the like. In this example, the aforementioned tissue is brain tissue, the tissue representation is a virtual model of the skull and the brain, the reference markers are tacks, an alignment guide assembles to the tacks, a biopsy needle is used as a tool, and the targeted axis is an axis extending from the tissue to be biopsied (i.e., a specific target location) and out through the skull where the brain will be exposed.

A medical plan may be generated as previously described. Planning software is used to define a targeted axis relative to a virtual model of the brain. The location of the tissue to be biopsied is also defined along the axis. A first virtual plane and a second virtual plane are then defined, where the planes intersect at the targeted axis. The medical plan is saved and transferred/uploaded to a computer-assisted medical system in the procedure room.

A tracking array is fixed to the skull, and the medical plan is registered to the actual location of the patient's skull in the procedure room using registration techniques known in the art.

After the medical plan is registered to the skull, the 2-DoF device 102 assembles a first tack and a second tack to the skull and coincident with the first virtual plane as previously described. An alignment guide (e.g., guide clamp 312) is then clamped onto the first tack and second tack, thereby forming a slot between the first tack and the second tack.

A biopsy needle actuated by the 2-DoF device 102 is then aligned with the targeted axis in the following manner. The user may first signal to the computing system 104 to change the plane that the 2-DoF device targets (i.e., change from the first virtual plane to the second virtual plane) using an input mechanism such as a trigger, button, or foot pedal. The user then moves the 2-DoF device 102 to align the biopsy needle in the slot formed by the alignment guide, and the control system actuates the working portion 204 of the 2-DoF device 102 relative to the hand-held portion 202 so as to align the biopsy needle coincident with the second virtual plane. The biopsy needle is then aligned with the targeted axis when the biopsy needle is coincident with the second virtual plane (by way of the actuation of the working portion 204 relative to the hand-held portion 202) and the first virtual plane (by way of the slot formed by the alignment guide). With the biopsy needle aligned with the targeted axis, the biopsy needle is advanced into the brain. A graphical user interface (GUI) may be used to display the location of the needle in the brain in real-time. The GUI may also display the specific tissue location to be biopsied relative to the biopsy needle. Once the biopsy needle reaches the location, the tissue is retrieved through the needle.

It should be appreciated that the above procedure to retrieve tissue for a biopsy may likewise be used to administer medications or other injectables to tissues in the brain and other areas of the body such as the spine, eye, heart, etc.

In the event two tissue locations need to be biopsied in the brain, three planes may be defined to permit the 2-DoF device 102 to target each location. For example, with reference again to FIG. 3B, the user may define a first targeted axis 307a to reach a first tissue location along the first targeted axis 307a, and a second targeted axis 307b to reach a second tissue location along the second targeted axis 307b. Three planes (304, 305, and 306) may be defined relative to the first target axis 307a and second target axis 307b to permit the 2-DoF device 102 to target the first tissue location with the aid of planes 304 and 306, and the second tissue location with the aid of planes 305 and 306.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A system for aligning a tool with a targeted axis in tissue to perform a medical procedure, the system comprising:
   a hand-held device comprising:
   a working portion movably connected to a hand-held portion, wherein the working portion is configured to (i) couple with a reference marker, and (ii) couple with a tool;
   and
   an actuator for moving the working portion relative to the hand-held portion in response to control signals; and
   a computing system comprising one or more processors configured to:
   determine a location of a first virtual plane, a second virtual plane, and a targeted axis, wherein the targeted axis has a pre-determined location coincident with an intersection axis of the first virtual plane and the second virtual plane;
   generate first control signals to maintain alignment of an axis of the reference marker, when coupled to the working portion, coincident with the first virtual plane for inserting the reference marker in the tissue coincident with the first virtual plane; and
   generate second control signals to maintain alignment of an axis of the tool, when coupled to the working portion, coincident with the second virtual plane; and
   wherein the reference marker and the alignment of the tool coincident with the second virtual plane are used to align the tool along the targeted axis.

2. The system of claim 1 further comprising a medical plan comprising a pre-determined location for the first virtual plane, a pre-determined location for the second virtual plane, and the pre-determined location for the targeted axis.

3. The system of claim 1 wherein the first control signals maintain alignment of an axis of a second reference marker coincident with the first virtual plane for inserting the second reference marker in the tissue coincident with the first virtual plane, wherein the reference marker and the second reference marker are laterally offset from one another.

4. The system of claim 3 further comprising an alignment guide configured to be mounted onto the reference marker and the second reference marker inserted in the tissue and dimensioned to receive at least a portion of the tool and constrain movement of the tool along the first virtual plane.

5. The system of claim 4 wherein the tissue is bone and the medical procedure is the formation of a tunnel in a bone, wherein the targeted axis is a central longitudinal axis of the tunnel.

6. The system of claim 5 wherein the tool is a third reference marker configured to be inserted coincident with the planned position for the targeted axis.

7. The system of claim 6 further comprising a hollow drill bit coupled to a second drill, wherein the hollow drill bit slides onto the third reference marker to guide the formation of the tunnel in the bone.

8. The system of claim 1 wherein the tool is at least one of a pin, a screw, a reference marker, a drill bit, a reamer, a mill, a cutter, a saw, a probe, a tissue remover, forceps, a needle, a laser, a radio-frequency emitter, an ablation instrument, a water-jet, or a cannula.

9. A method for aligning a tool with a targeted axis in tissue to perform a medical procedure, the method comprising:
   determining a location of a first virtual plane, a second virtual plane, and a targeted axis, wherein the targeted axis has a pre-determined location coincident with an intersection axis of the first virtual plane and the second virtual plane;
   generating first control signals for a robotic device to maintain alignment of an axis of a first reference marker, when coupled to the robotic device, coincident with the first virtual plane for inserting the first reference marker in the tissue coincident with the first virtual plane; and
   generating second control signals for the robotic device to maintain alignment of an axis of a tool, when coupled to the robotic device, coincident with the second virtual plane, wherein the first reference marker and the alignment of the tool coincident with the second virtual plane are used to align the tool along the targeted axis.

10. The method of claim 9 further comprising generating third control signals for the robotic device to maintain alignment of an axis of a second reference marker, when coupled to the robotic device, coincident with the first virtual plane for inserting the second reference marker in the tissue coincident with the first virtual plane and laterally offset from the first reference marker.

11. The method of claim 10 further comprising providing an alignment guide configured to be mounted onto the first reference marker and the second reference marker inserted in the tissue and dimensioned to receive at least a portion of the tool and constrain movement of the tool along the first virtual plane while the robotic device maintains alignment of the tool coincident with the second virtual plane.

12. The method of claim 9 wherein the robotic device comprises: a working portion movably connected to a hand-held portion, wherein the working portion is configured to (i) couple with the first reference marker, and (ii) couple with the tool; and an actuator for moving the working portion relative to the hand-held portion in response to control signals.

13. The method of claim 9 wherein the tool is a third reference marker configured to be inserted coincident with the pre-determined location for the targeted axis.

14. The method of claim 13 further comprising a hollow drill bit coupled to a second drill, wherein the hollow drill bit slides onto the third reference marker to guide formation of a tunnel in the tissue.

15. The method of claim 9 wherein the tool is at least one of a pin, a screw, a reference marker, a drill bit, a reamer, a mill, a cutter, a saw, a probe, a tissue remover, forceps, a needle, a laser, a radio-frequency emitter, an ablation instrument, a water-jet, or a cannula.

\* \* \* \* \*